US009867557B2

(12) United States Patent
Ohzawa et al.

(10) Patent No.: US 9,867,557 B2
(45) Date of Patent: Jan. 16, 2018

(54) PROBE

(71) Applicant: KONICA MINOLTA, INC., Chiyoda-ku (JP)

(72) Inventors: Soh Ohzawa, Osaka (JP); Shoichi Tao, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 635 days.

(21) Appl. No.: 14/385,466

(22) PCT Filed: Feb. 14, 2013

(86) PCT No.: PCT/JP2013/000815
§ 371 (c)(1),
(2) Date: Sep. 15, 2014

(87) PCT Pub. No.: WO2013/136664
PCT Pub. Date: Sep. 19, 2013

(65) Prior Publication Data
US 2015/0045678 A1 Feb. 12, 2015

(30) Foreign Application Priority Data

Mar. 13, 2012 (JP) .................. 2012-055673

(51) Int. Cl.
| A61B 5/107 | (2006.01) |
| A61B 5/00 | (2006.01) |
| G02B 23/24 | (2006.01) |
| A61B 1/00 | (2006.01) |
| A61B 1/015 | (2006.01) |
| A61B 1/07 | (2006.01) |

(52) U.S. Cl.
CPC ........ *A61B 5/1079* (2013.01); *A61B 1/00009* (2013.01); *A61B 1/00039* (2013.01); *A61B 1/00052* (2013.01); *A61B 1/015* (2013.01); *A61B 1/07* (2013.01); *A61B 5/0084* (2013.01); *A61B 5/1076* (2013.01); *G02B 23/24* (2013.01); *A61B 5/0071* (2013.01); *A61B 5/0075* (2013.01); *A61B 2562/146* (2013.01); *A61B 2562/168* (2013.01)

(58) Field of Classification Search
CPC ... A61B 5/1079; A61B 5/0084; A61B 5/1076; A61B 1/00009; A61B 1/00039; A61B 1/015
See application file for complete search history.

(56) References Cited

U.S. PATENT DOCUMENTS

2003/0191398 A1 10/2003 Motz et al.
2004/0260149 A1 12/2004 Ishibiki
2012/0190990 A1 7/2012 Ohzawa et al.

FOREIGN PATENT DOCUMENTS

| CN | 1638686 | 7/2005 |
| CN | 102469920 | 5/2012 |
| JP | 8-278456 | 10/1996 |
| JP | 2003-250753 | 9/2003 |
| JP | 2003-262774 | 9/2003 |
| JP | 2005-6822 | 1/2005 |

(Continued)

*Primary Examiner* — Joseph Dietrich
(74) *Attorney, Agent, or Firm* — Cozen O'Connor

(57) ABSTRACT

At the leading end of a probe (11) is provided a holding part (56) that has a space (60) having an inner diameter smaller than the inner diameter of the probe (11). A liquid discharge groove (61) that communicates between the space (60) and the outer peripheral side surface of the holding part (56) is formed in the holding part (56).

9 Claims, 19 Drawing Sheets

(56) References Cited

FOREIGN PATENT DOCUMENTS

| | | |
|---|---|---|
| JP | 2005-522293 | 7/2005 |
| JP | 2006-325816 | 12/2006 |
| JP | 2008-206559 | 9/2008 |
| JP | 2010-131120 | 6/2010 |
| WO | WO 2011/162342 | 12/2011 |

PROBE

RELATED APPLICATIONS

This is a U.S. National stage of International application No. PCT/JP2013/000815 filed on Feb. 14, 2013.

This patent application claims the priority of Japanese application no. 2012-055673 filed Mar. 13, 2012 the disclosure content of which is hereby incorporated by reference.

TECHNICAL FIELD

The present invention relates to a probe for use in examining for a lesion such as cancer and its progression by irradiating a measurement object part in a lumen with light and by obtaining measurement light radiated from the measurement object part.

BACKGROUND ART

Currently, observation and diagnosis of a body lumen using electron endoscopes is a widely accepted diagnosis method. In such a diagnosis method, since body tissues are directly observed, a lesion is not required to be removed, and the burden on examinees is small. Further, in recent years, other than the so-called video scope, there have been proposed diagnosis devices and ultrasound devices based on various optical principles, and some of such devices have been practically used. As above, new measurement principles have been adopted, and different measurement principles have been combined.

In particular, it is known that information which cannot be obtained by simply seeing an image of a body tissue can be obtained by observing and measuring fluorescence from a body tissue or fluorescence from a fluorescence material applied to a tissue. A fluorescence image endoscope system has been proposed in which a fluorescence image is acquired and displayed with a visible image in an overlapped manner. Such a system serves to an early detection of a malignant tumor, and is therefore very promising.

In addition, methods are known in which a state of a body tissue is determined by acquiring information on the strength of a fluorescence without forming a fluorescence image. In such methods, fluorescence is typically acquired without using an imaging device mounted in an electron endoscope.

Examples of a diagnostic tool for the fluorescence diagnosis, that is, examples of a probe, includes one which enters the body via a forceps channel of an endoscope, and one which is integral with an endoscope.

Generally, such probes include a first optical fiber group that guides light applied to a body tissue and a second optical fiber group that guides light emitted from the body tissue, or includes a fiber group that serves the roles of the first and second optical fiber groups.

A probe has a configuration in which one side (distal end side) thereof to be inserted into the body in such a manner as to face a biological tissue faces the tissue through an optical window member such as a slide glass and an optical device such as a lens. This configuration, however, involves a risk that, when the probe is inserted into the body, the distal end of the probe makes close contact with a biological tissue at the time of irradiating a measurement object part with excitation light, and consequently, the optical window member and the optical device drop off from the probe and remain in the body.

Under such circumstances, a technique has been proposed in which a holding section that holds the optical window member and the optical device from the distal end side of the probe (see, for example, PTL 1). In the technique disclosed in PTL 1, as illustrated in FIG. 19, catch 120 that catches optical device 100 is formed in holding section 110 that holds optical device 100 at the probe distal end side, thereby preventing optical device 100 from dropping off from the probe.

However, such a configuration has the following problem. Specifically, by the thickness of catch 120, space 130 is defined between distal end surface 125 of optical device 100 and a measurement object part of biological tissue 120. Thus, the configuration involves a risk that liquid such as water, blood and bodily fluid on the surface of biological tissue 120 enters space 130, and remains in space 130, for example. When liquid remains in space 130 in this manner, measurement results obtained by the probe may be negatively influenced depending on the kind of the remaining liquid.

In relation to the above-mentioned problem, the techniques disclosed in PTLS 2 and 3 have been proposed. The technique disclosed in PTL 2 is a technique to prevent liquid remaining at an observation window from staying at the side wall end due to the surface tension even when the liquid is evaporated and diffused by supplying air and water from an air-and-water supply nozzle provided at a distal end surface of an endoscope. To be more specific, in a direction of the space of the air-and-water supply nozzle, surface tension fracturing means (for example a plurality of trenches) that fractures the surface tension of liquid emitted by the air-and-water supply nozzle is provided. Thus, it is possible to ensure favorable visibility at the observation window after air and water are supplied.

The technique disclosed in PTL 3 is a technique to effectively remove a foreign matter such as bodily fluid adhered in a film form on the surface of an object lens provided at the distal end surface of an endoscope by jetting cleaning solution such as water onto the surface of an object lens from a water supply nozzle. To be more specific, vibration applying means that applies minute vibration is provided at the distal end portion of the endoscope. This makes it easy to peel from the lens surface the foreign matter adhered in a film form on the surface of the object lens.

CITATION LIST

Patent Literature

PTL 1
Japanese Unexamined Patent Application Publication (Translation of PCT Application) No. 2005-522293
PTL 2
Japanese Patent Application Laid-Open No. 2010-131120
PTL 3
Japanese Patent Application Laid-Open No. 8-278456

SUMMARY OF INVENTION

Technical Problem

Although the techniques disclosed in PTLS 2 and 3 can be applied at a place where a large area can be ensured such as the distal end side of an endoscope, but cannot be easily applied as it is at a place having a small diameter where a large area cannot be easily ensured, such as the distal end side of a probe.

An object of the present invention is to provide a probe which can prevent liquid from remaining in a space defined between an optical member and a measurement object part of a biological tissue.

Solution to Problem

A probe according to an embodiment of the present invention is a prove in which an optical member is fitted in a distal end of a tubular member that is insertable to a lumen, the probe being configured to irradiate a measurement object part in the lumen with light and to acquire measurement light radiated from the measurement object part, wherein a holding section including a space having an internal diameter smaller than an internal diameter of the tubular member is provided at the distal end of the tubular member, and a liquid ejection trench configured to connect the space and an outer periphery surface of the holding section is formed in the holding section.

Advantageous Effects of Invention

According to the present invention, it is possible to prevent liquid from remaining in a space defined between an optical member and a measurement object part of a biological tissue.

DESCRIPTION OF EMBODIMENTS

Figure 1:
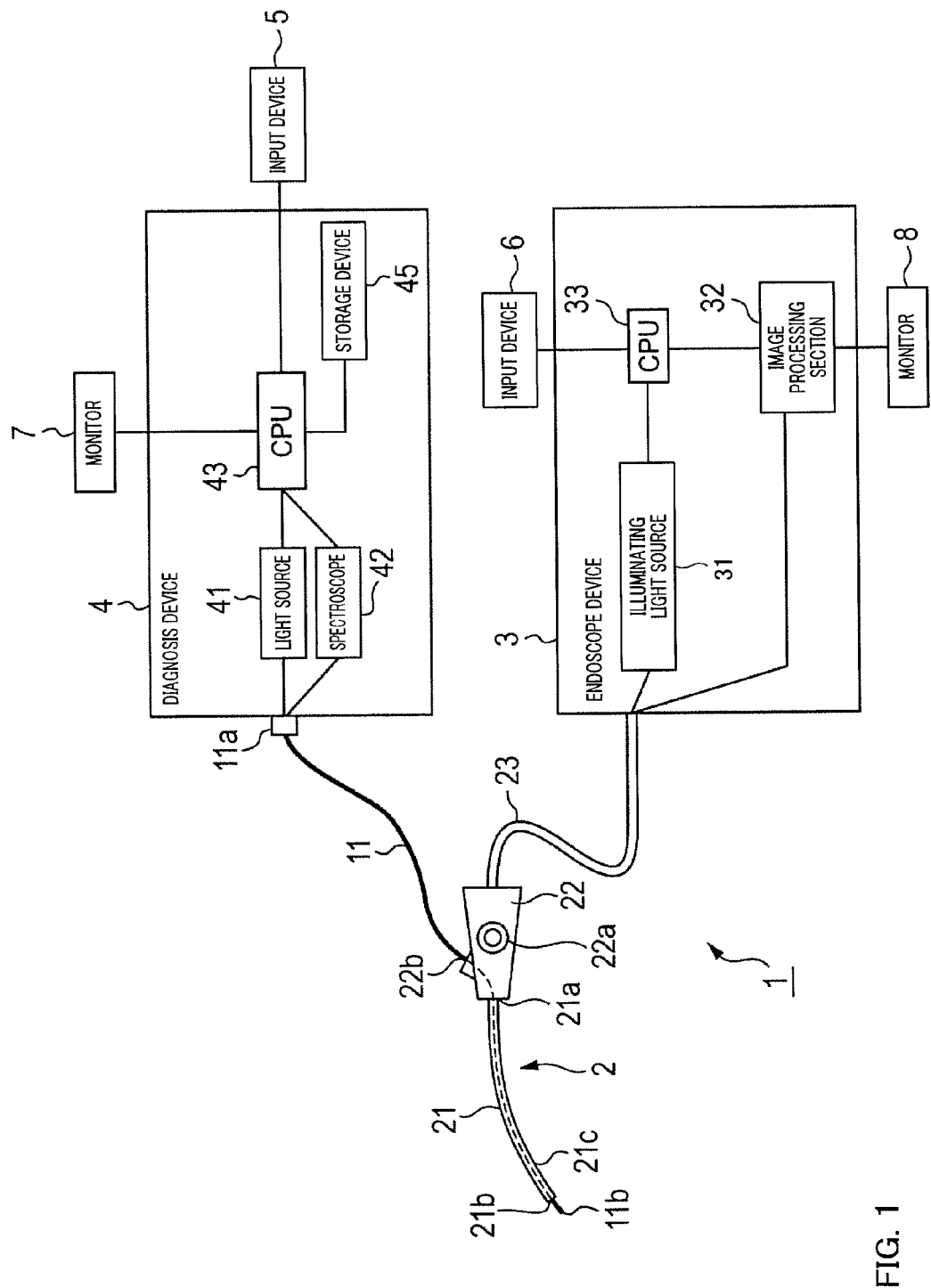
FIG. 1 illustrates a configuration of an endoscope system according to an embodiment of the present invention.

In the following, an embodiment of the present invention is described in detail with reference to the accompanying drawings. Endoscope system 1 illustrated in FIG. 1 includes endoscope main body 2, endoscope device 3 and diagnosis device 4.

Endoscope main body 2 includes long flexible introduction portion 21 which is formed so as to be capable of being introduced into body lumen, operation section 22 provided at proximal end portion 21a of introduction portion 21, and cable 23 that communicably connects introduction portion 21 with endoscope device 3 via operation section 22.

Introduction portion 21 has, over substantially the entire length thereof, such a flexibility that it can be readily bent to follow the curvature of the lumen when it is advanced in the lumen. In addition, introduction portion 21 has a mechanism (not illustrated) that can curve a part (operable section 21c) of distal end portion 21b in a certain range at any angle in accordance with operation from nob 22a of operation section 22.

Figure 2:
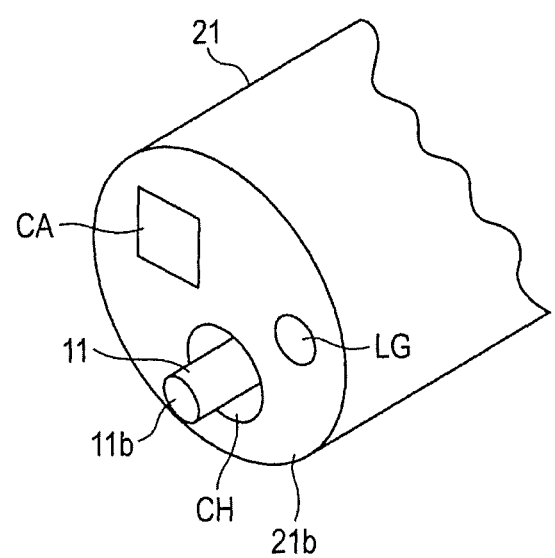
FIG. 2 is a perspective view of a distal end portion of an endoscope main body according to the embodiment of the present invention.

As illustrated in FIG. 2 which is a perspective view of distal end portion 21b, introduction portion 21 includes camera CA, light guide LG, forceps channel CH and an air-and-water supply nozzle which is not illustrated in the drawing.

Light guide LG guides illuminating light (visible light) emitted by illuminating light source 31 of endoscope device 3 to distal end portion 21b, and outputs the illuminating light from distal end portion 21b.

Camera CA is an electron camera including a solid imaging device. Camera CA captures an image of a region in a lumen (observation object part) illuminated with illuminating light emitted from light guide LG, and transmits the imaging signal to endoscope device 3.

Forceps channel CH is an inner cavity having a diameter of 2.6 mm which is formed in operation section 22 in such a manner as to communicate with introduction portion 21 formed in inlet 22b. To forceps channel CH, various devices for observation, diagnosis, and operation of a lesion and the like can be inserted. In the present embodiment, as illustrated in FIG. 1, it is possible to insert probe 11 that irradiates a measurement object part in a lumen with light and acquires measurement light radiated from the measurement object part to thereby examine whether lesion such as cancer is present and the progression of the lesion.

As illustrated in FIG. 1, probe 11 is a long flexible pipe member extending from probe proximal end portion 11a to probe distal end portion 11b. Probe 11 is connected with diagnosis device 4 via a connector provided in probe proximal end portion 11a.

Next, a configuration of diagnosis device 4 will be described. Diagnosis device 4 includes light source 41, spectroscope 42, CPU (Central Processing Unit) 43 that functions as a diagnosis section and storage device 45. Diagnosis device 4 is connected with input device 5 and monitor 7 that functions as an output section.

Input device 5 inputs a user's instruction for diagnosis device 4. In the present embodiment, input device 5 is composed of, for example, a keyboard, mouse, switch or the like. Monitor 7 receives image data output from diagnosis device 4 to display various kinds of images.

Light source 41 emits excitation light such as xenon light when input device 5 receives an instruction to execute an examination process of a biological tissue of a measurement object part (for example, a lesion) in a lumen. When inserted in forceps channel CH and introduced in a lumen, probe 11 guides excitation light emitted from light source 41, and emits the light as light for examining a measurement object part. In addition, probe 11 receives measurement light from a measurement object part as biological information of the measurement object part, and guides the light to spectroscope 42 of diagnosis device 4. The present embodiment adopts fluorescence spectroscopy as a method for receiving measurement light from a measurement object part.

Spectroscope 42 performs a spectrum analysis on the measurement light guided by probe 11 from the measurement object part. On the basis of results of the spectrum analysis of spectroscope 42, CPU 43 performs a diagnosis to determine whether a lesion presents in the measurement object part in a lumen and to determine the kind of the lesion. Then, CPU 43 outputs image data representing the results of the diagnosis to monitor 7, to thereby display an image of the results of the diagnosis on monitor 7. By visually confirming the image of the results of the diagnosis displayed on monitor 7, the user can evaluate the expansion of the lesion and the degree of the disease.

Storage device 45 is a HDD (Hard Disk Drive) and the like built in diagnosis device 4. Storage device 45 stores the results of the diagnosis of CPU 43 and the like. It is to be noted that storage device 45 may not be built in diagnosis device 4, and may be externally provided to diagnosis device 4. Alternatively, storage device 45 may exist on the communication network.

Next, a configuration of endoscope device 3 will be described. Endoscope device 3 includes illuminating light source 31, image processing section 32 and CPU 33. Endoscope device 3 is connected with input device 6 and monitor 8.

Input device 6 receives a user's instruction for endoscope device 3. In the present embodiment, endoscope device 3 is composed of a keyboard, mouse, switch or the like, for example. Monitor 7 inputs image data output from diagnosis device 4 to display various kinds of images.

Illuminating light source 31 supplies illuminating light to light guide LG by emitting illuminating light in order to illuminate an observation object part in a lumen.

Image processing section 32 receives an imaging signal from endoscope main body 2, and performs a predetermined signal processing on the imaging signal, and then, outputs the processed signal to monitor 8 as an endoscope video signal. In this manner, an endoscope image, based on endoscope video signal is displayed on a screen of monitor 8. That is, when an image of an observation object part in a lumen is captured, the image is displayed on monitor 8. CPU 33 controls operations of illuminating light source 31 and image processing section 32.

Figure 3:
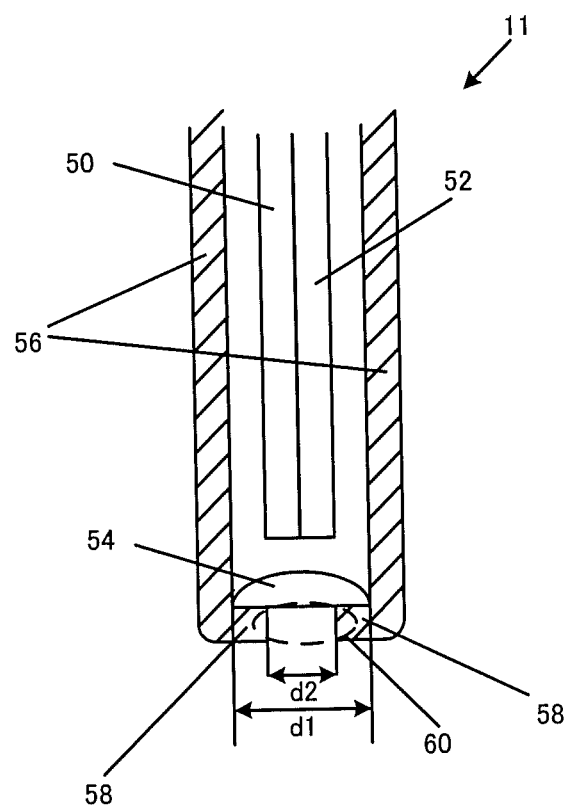
FIG. 3 illustrates a configuration of a probe according to the embodiment of the present invention.

FIG. 3 illustrates a configuration of the distal end side of probe 11 (which is also referred to as "pipe," the same shall apply hereinafter). As illustrated in FIG. 3, probe 11 includes therein excitation light fiber 50, light receiving fiber 52, and lens 54 that functions as an optical member. Although not shown in the drawing, probe 11 may include an optical filter that selectively transmits or blocks excitation light.

Lens 54 is a hemispherical condenser lens having a positive refractive power. Lens 54 is fitted in front of excitation light fiber 50 and light receiving fiber 52 in such a manner that lens 54 faces the distal end side of probe 11 and that the optical axis of lens 54 matches the central axis of probe 11. It is to be noted that lens 54 may be composed of conventionally known lenses which have a non-hemispherical form.

Excitation light fiber 50 irradiates a measurement object part with excitation light emitted from light source 41. Light receiving fiber 52 receives, as measurement light, fluorescence which has generated by the measurement object part or by a medicine injected in advance to the measurement object part in response to excitation light output from excitation light fiber 50. It is to be noted that the measurement light from the measurement object part may be diffusing light or Raman scattering light, not fluorescence. In the present embodiment, probe 11 includes a plurality of light receiving fibers 52.

Further, in probe 11, catch 58 that catches lens 54 is formed in holding section 56 that holds lens 54 at the distal end side of probe 11, whereby lens 54 is prevented from dropping off from probe 11. At the distal end of probe 11, catch 58 of holding section 56 has a space having internal diameter d2 (for example, 1.35 mm) smaller than internal diameter d1 (for example, 2.6 mm) of probe 11. The space has a depth of, for example, 0.3 mm.

Figure 4A:
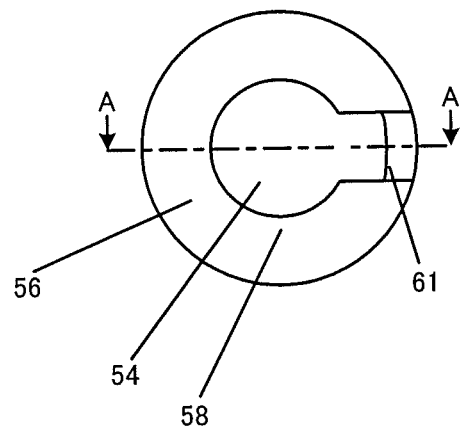
FIGS. 4A and 4B illustrate a configuration of a probe distal end portion according to the embodiment of the present invention.
Figure 4B:
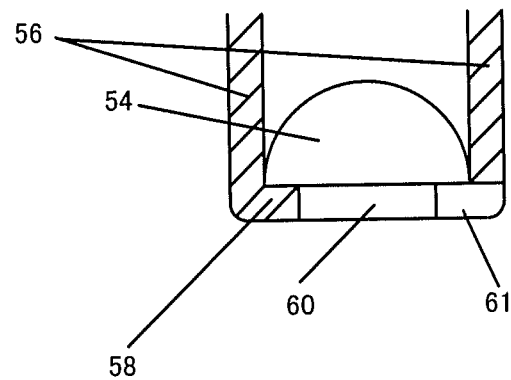

FIG. 4A illustrates probe 11 as viewed from the distal end side of probe 11. FIG. 4B is a sectional view taken along line A-A of FIG. 4A. As illustrated in FIG. 4A and FIG. 4B, one liquid ejection trench 61 that connects space 60 and an outer periphery surface of holding section 56 of probe 11 is formed. Liquid ejection trench 61 has, for example, a width of 0.3 mm, and a depth of 0.3 mm. Thus, a path from which liquid having entered space 60 is discharged out of space 60 can be ensured.

Figure 5A:
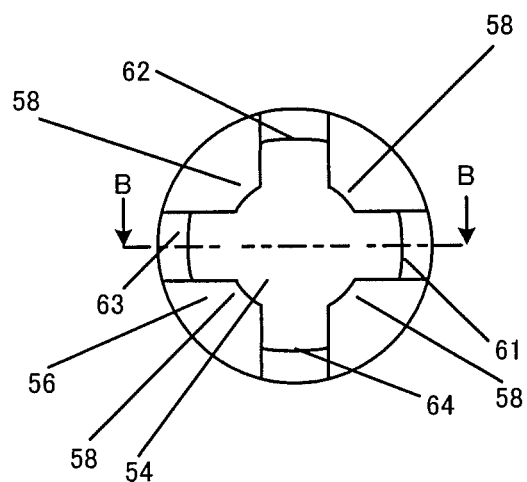
FIGS. 5A and 5B illustrate a configuration of the probe distal end portion according to the embodiment of the present invention.
Figure 5B:
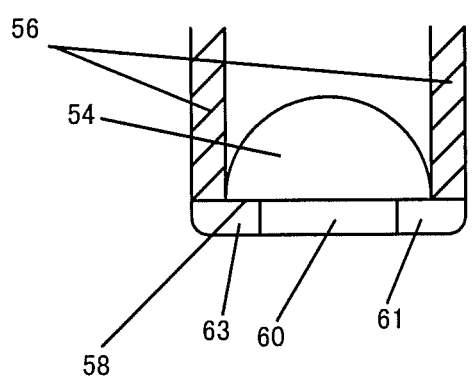

It is to be noted that the number and width of the liquid ejection trenches that connect space 60 and the outer periphery surface of holding section 56 are not limited to the example illustrated in FIGS. 4A and 4B. For example, as illustrated in FIG. 5A and FIG. 5B, it is also possible to form four liquid ejection trenches 61, 62, 63 and 64 that connect space 60 and the outer periphery surface of holding section 56 at 90-degree intervals. In addition, the corners and sides of liquid ejection trenches 61, 62, 63 and 64 may be chamfered.

In view of facilitating the discharge of liquid in space 60, each of liquid ejection trenches 61, 62, 63 and 64 desirably has a wide width. This is because liquid cannot easily flow in liquid ejection trenches 61, 62, 63 and 64 due to the surface tension when liquid ejection trenches 61, 62, 63 and 64 each has a small width. Therefore, in the case where the liquid ejection trenches have the same area, a small number of wide liquid ejection trenches are preferable to a large number of thin liquid ejection trenches.

As has been described in detail, in the present embodiment, holding section 56 provided with space 60 having an internal diameter smaller than the internal diameter of probe 11 is provided at the distal end of probe 11, and liquid ejection trenches 61, 62, 63 and 64 that connect space 60 and the outer periphery surface of holding section 56 are formed in holding section 56. According to the above-mentioned configuration of the present embodiment, in the case where the distal end of probe 11 makes close contact with a biological tissue at the time of irradiating a measurement object part with excitation light, when the biological tissue enters space 60, liquid having entered space 60 can be ejected out of space 60 through liquid ejection trenches 61, 62, 63 and 64. This makes it possible to prevent liquid from remaining in space 60 defined between lens 54 and the measurement object part of the biological tissue, and thus, measurement results of probe 11 is prevented from being influenced by the liquid.

In addition, in the present embodiment, the act of bringing probe distal end portion 11b into contact with a biological tissue serves to diffuse liquid, and serves as the driving force for discharging the liquid when the biological tissue enters space 60. Therefore, it is not necessary to additionally provide complicated mechanisms such as a vibration mechanism and a nozzle to achieve the liquid diffusion function. In addition, while probe distal end portion 11b is composed of catch 58 that holds lens 54, catch 58 can sufficiently maintain the drop-off prevention function even when liquid ejection trenches 61, 62, 63 and 64 are provided in places.

Figure 6A:
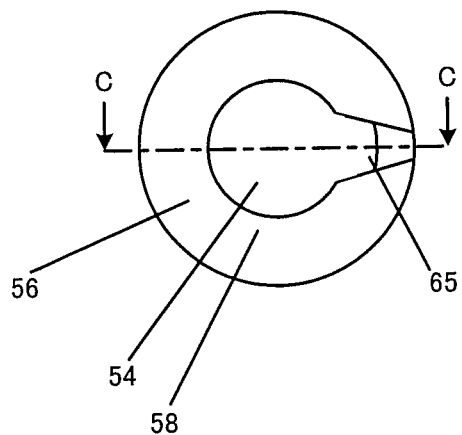
FIGS. 6A and 6B illustrate a modification of the configuration of the probe distal end portion according to the embodiment of the present invention.
Figure 6B:
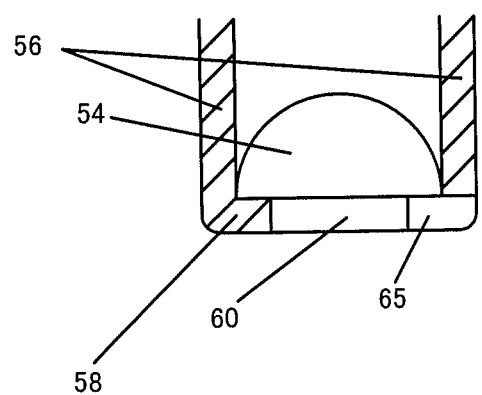
Figure 7A:
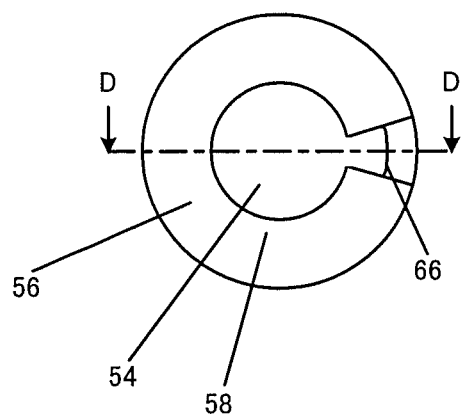
FIGS. 7A and 7B illustrate a modification of the configuration of the probe distal end portion according to the embodiment of the present invention.
Figure 7B:
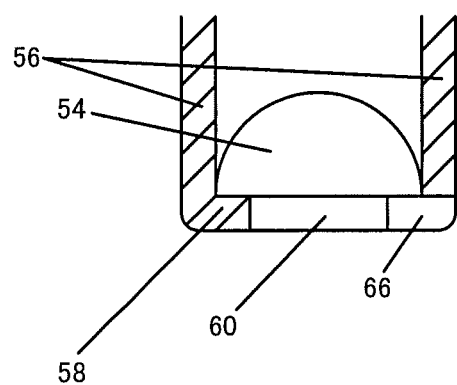

It is to be noted that, in the above-mentioned embodiment, as illustrated in FIG. 6A and FIG. 6B, liquid ejection trench 65 may have a tapered form whose width decreases from space 60 side toward the outer periphery surface of holding section 56. Alternatively, as illustrated in FIG. 7A and FIG. 7B, liquid ejection trench 66 may have a tapered form whose width increases from space 60 side toward the outer periphery surface of holding section 56. In view of facilitating the outflow of liquid from space 60, liquid ejection trench 65 preferably has a tapered form whose width decreases from space 60 side toward the outer periphery surface of holding section 56.

Figure 8A:
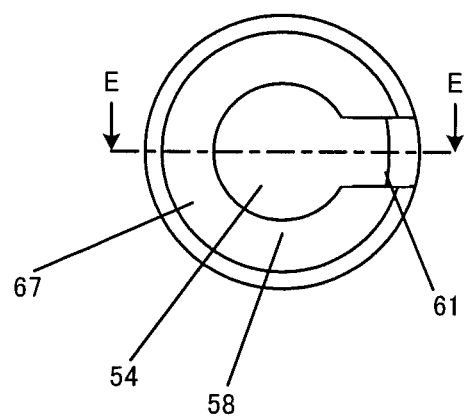
FIGS. 8A and 8B illustrate a modification of the configuration of the probe distal end portion according to the embodiment of the present invention.
Figure 8B:
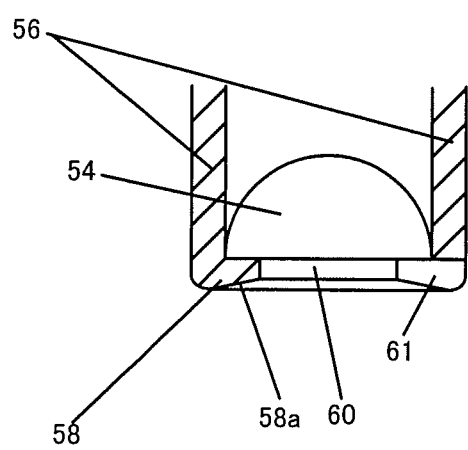

In addition, in the above-mentioned embodiment, as illustrated in FIG. 8A and FIG. 8B, a tapered surface having a dent form whose depth increases toward the inside in the radial direction of probe 11 may be provided to surface 58a that faces a measurement object part in holding section 67. With this configuration, when probe distal end portion 11b makes contact with a biological tissue, the biological tissue easily enters space 60, and the liquid diffusion function by the biological tissue can be sufficiently achieved.

Figure 9A:
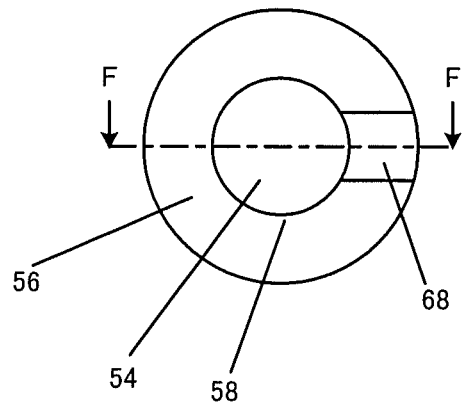
FIGS. 9A and 9B illustrate a modification of the configuration of the probe distal end portion according to the embodiment of the present invention.
Figure 9B:
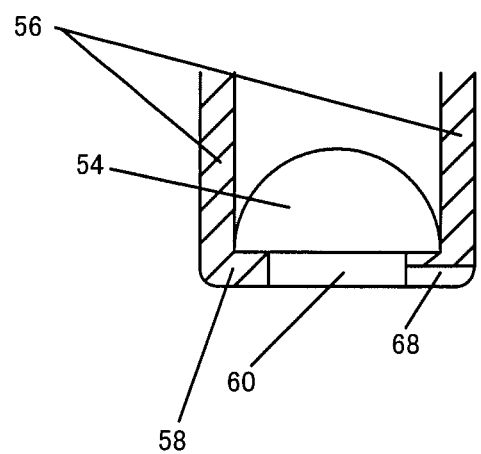

In addition, in the above-mentioned embodiment, as illustrated in FIG. 9A and FIG. 9B, liquid ejection trench 68 whose bottom does not reach the end surface of lens 54 may be formed in holding section 56. To discharge liquid remaining in space 60, the bottom part of liquid ejection trench is desirably adjacent to the end surface of lens 54. Meanwhile, holding section 56 has a role to ensure the liquid-tightness or air-tightness in probe 11 so as to prevent liquid from infiltrating to probe 11, as well as a role to prevent the drop off of lens 54. Therefore, a configuration in which the liquid ejection trench portion occupies a large part of the distal end portion of probe 11. For this reason, in the present modification, liquid ejection trench 68 whose bottom portion does not reach the end surface of lens 54 is provided to holding section 56, whereby the contact area between holding section 56 and lens 54 increases, lens 54 can be further brought into close contact with holding section 56, and the liquid-tightness or air-tightness in probe 11 can be securely ensured.

Figure 10A:
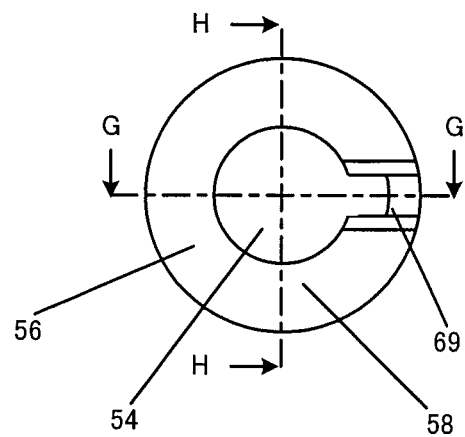
FIGS. 10A to 10C illustrate a modification of the configuration of the probe distal end portion according to the embodiment of the present invention.
Figure 10B:
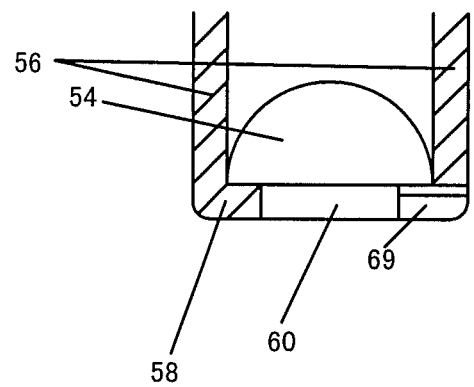
Figure 10C:
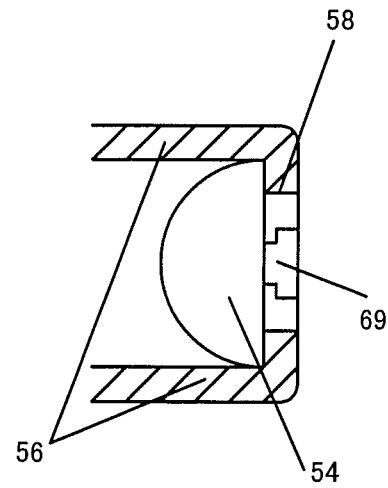

In addition, in the above-mentioned embodiment, as illustrated in FIGS. 10A to 10C, in the bottom portion of liquid ejection trench 69, a stepped groove whose depth increases toward the center portion in the width direction of liquid ejection trench 69 may be continuously formed along the extending direction of liquid ejection trench 69. FIG. 10A illustrates probe 11 as viewed from the distal end side of probe 11. FIG. 10B is a sectional view taken along line G-G of FIG. 10A. FIG. 10C is a sectional view taken along line H-H of FIG. 10A. This configuration makes it possible to ensure a large contact area between lens 54 and holding section 56 while ensuring a wide width of the entire liquid ejection trench 69. Hence, the liquid-tightness or air-tightness in probe 11 can be ensured while facilitating the flow of liquid.

Figure 11A:
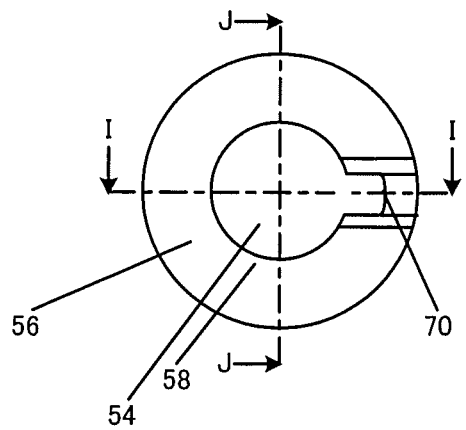
FIGS. 11A to 11C illustrate a modification of the configuration of the probe distal end portion according to the embodiment of the present invention.
Figure 11B:
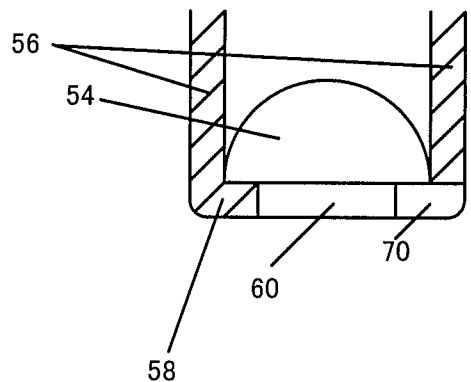
Figure 11C:
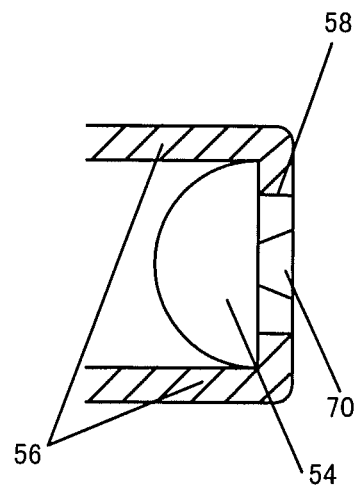

In addition, in the above-mentioned embodiment, as illustrated in FIGS. 11A to 11C, liquid ejection trench 70 may have a cross-sectional shape cut out in a V-shape whose width decreases toward the bottom portion. FIG. 11A illustrates probe 11 as viewed from distal end side of probe 11. FIG. 11B is a sectional view taken along line I-I of FIG. 11A. FIG. 11C is a sectional view taken along line J-J of FIG. 11A. With this configuration, a large contact area between lens 54 and holding section 56 can be ensured while ensuring a wide width of the entire liquid ejection trench 70. Hence, the liquid-tightness or air-tightness in probe 11 can be ensured while facilitating the flow of liquid.

Figure 12:
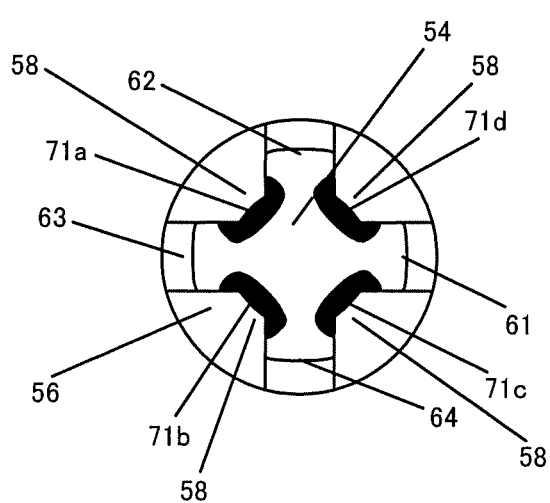
FIG. 12 illustrates behavior of liquid in a space in a case where a liquid ejection trench corresponding to FIGS. 5A and 5B is provided to a holding section.

FIG. 12 illustrates a behavior of liquid in space 60 in a case where liquid ejection trenches corresponding to FIGS. 5A and 5B is provided to holding section 56. As illustrated in FIG. 12, when a biological tissue enters space 60, liquid having entered space 60 can be ejected out of space 60 through liquid ejection trenches 61, 62, 63 and 64. However, liquids 71a, 71b, 71c and 71d remain at positions where liquid ejection trenches 61, 62, 63 and 64 are not provided. For this reason, when any of excitation light fiber 50 and light receiving fiber 52 is disposed at a position displaced from the optical axis of lens 54, an axial end portion of the fiber disposed at a displaced position is desirably disposed at a position corresponding to any of opening parts of liquid ejection trenches 61, 62, 63 and 64 on space 60 side of holding section 56.

Figure 13A:
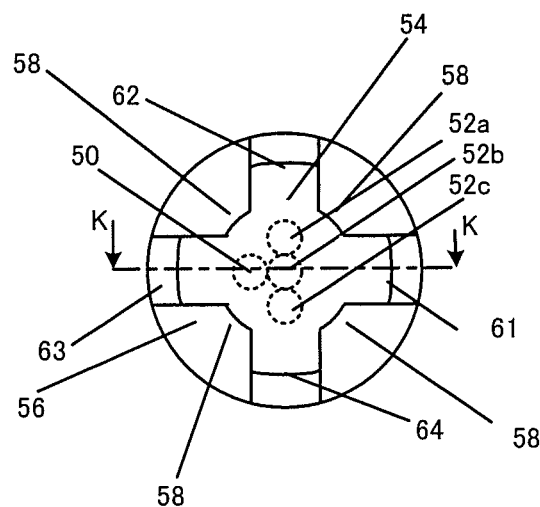
FIGS. 13A and 13B illustrate a positional relationship of an excitation light fiber, a light receiving fiber, and a liquid ejection trench.
Figure 13B:
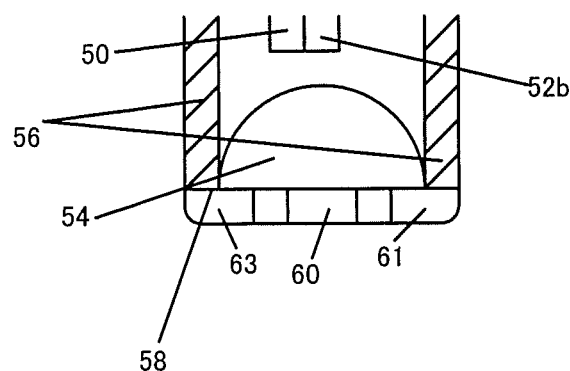
Figure 14A:
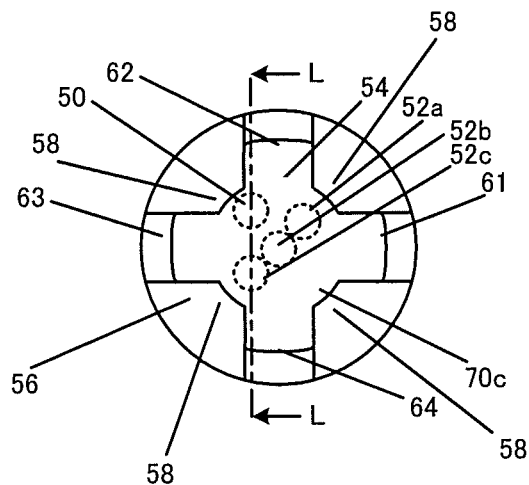
FIGS. 14A and 14B illustrate a positional relationship of the excitation light fiber, the light receiving fiber, and the liquid ejection trench.
Figure 14B:
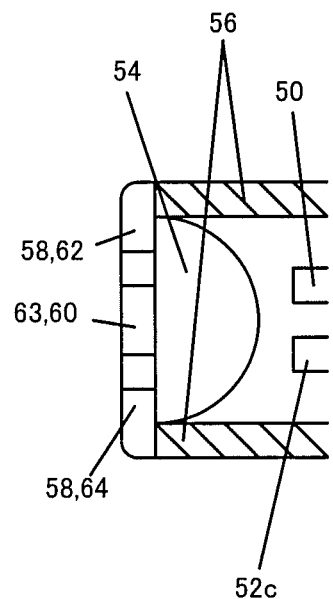

When excitation light fiber 50 and light receiving fiber 52 are required to be disposed at a position displaced from optical axis of lens 54, an axial end portion of excitation light fiber 50 and axial end portions of light receiving fibers 52a and 52c are desirably disposed at a position corresponding to an opening part of liquid ejection trench 63 on space 60 side of holding section 56 as illustrated in FIGS. 13A and 13B for example. The reason for this is as follows. In a case where the axial end portions of excitation light fiber 50 and light receiving fiber 52c are not disposed at positions corresponding to the opening parts of liquid ejection trenches 61, 62, 63 and 64 on space 60 side of holding section 56 as illustrated in FIGS. 14A and 14B, there is a high possibility that light hits liquid remaining at and around a place (that is, a place where the axial end portion of excitation light fiber 50 or light receiving fiber 52c is located) where liquid ejection trenches 61, 62, 63 and 64 are not provided, resulting in a risk that fluorescence from the liquid is observed at the time of a fluorescence measurement, for example.

In addition, in a case where three light receiving fibers 52a to 52c are disposed side by side in a certain direction as illustrated in FIGS. 13A and 13B, the axial end portions of light receiving fibers 52a to 52c are desirably disposed side by side at a position corresponding to the opening parts of liquid ejection trenches 62 and 64 on space 60 side of holding section 56, for the above-described reason.

Figure 15A:
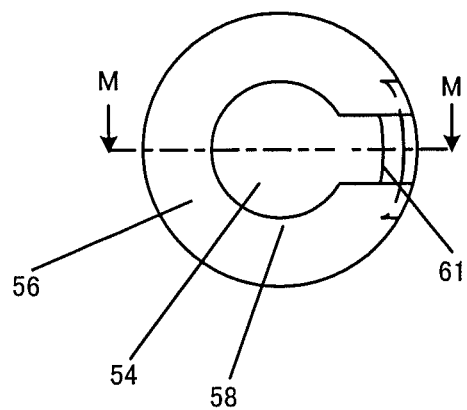
FIGS. 15A to 15C illustrate a modification of the configuration of the probe distal end portion according to the embodiment of the present invention.
Figure 15B:
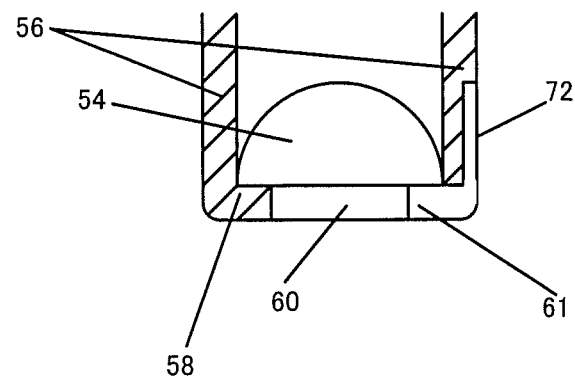
Figure 15C:
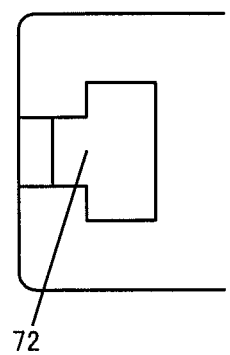
Figure 16A:
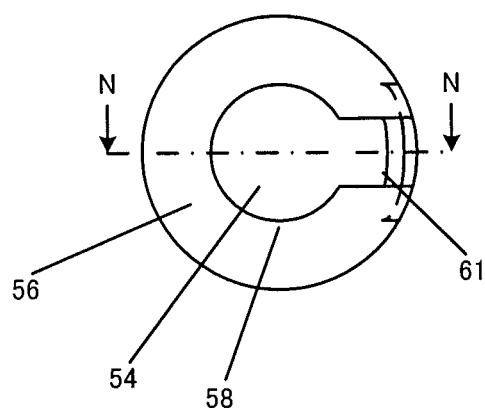
FIGS. 16A to 16C illustrates a modification of the configuration of the probe distal end portion according to the embodiment of the present invention.
Figure 16B:
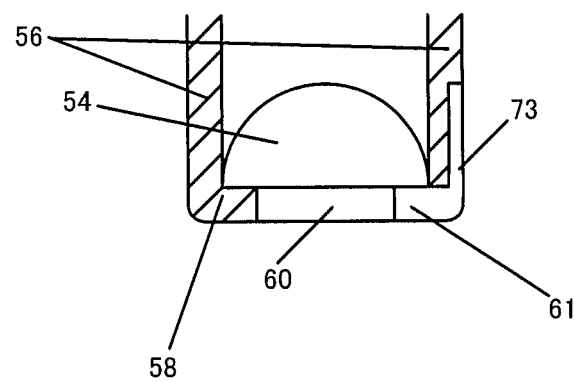
Figure 16C:
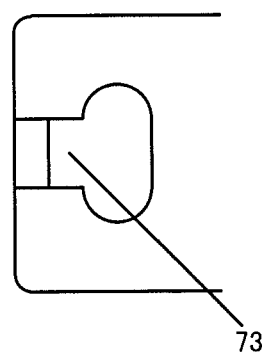

In addition, in the above-mentioned embodiment, holding section 56 may be provided with a liquid housing section in communication with liquid ejection trench 61. FIG. 15A illustrates probe 11 as viewed from the distal end side of probe 11. FIG. 15B is a sectional view taken along line M-M of FIG. 15A. FIG. 15C is a side view of holding section 56 of probe 11. As illustrated in FIGS. 15A to 15C, in the side surface of holding section 56, liquid housing section 72 in communication with liquid ejection trench 61 is formed. Liquid housing section 72 has a width greater than that of liquid ejection trench 61. Therefore, part of the liquid discharged from space 60 moves to and remains in liquid housing section 72, whereby it is possible to prevent the liquid from again returning back to space 60 due to the surface tension. Likewise, as illustrated in FIGS. 16A to 16C, holding section 56 may be provided with liquid housing section 73 in communication with liquid ejection trench 61.

Figure 17A:
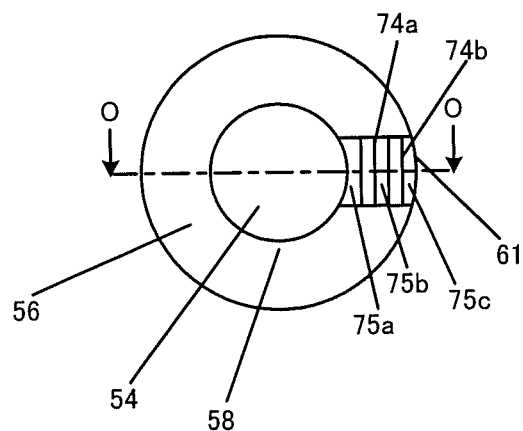
FIGS. 17A to 17C illustrate a modification of the configuration of the probe distal end portion according to the embodiment of the present invention.
Figure 17B:
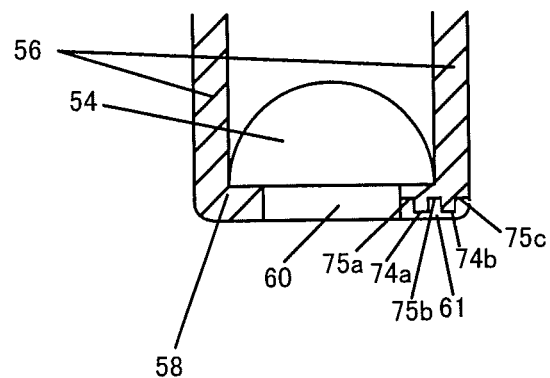
Figure 17C:
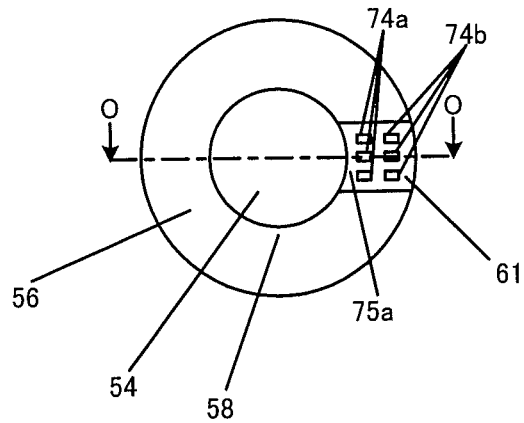

In addition, in the above-mentioned embodiment, as illustrated in FIGS. 17A to 17C, a protrusion and recess may be provided to the bottom surface of liquid ejection trench 61. In the configuration illustrated in FIGS. 17A and 17B, in the bottom surface of liquid ejection trench 61, ridge-shaped protrusions 74a and 74b, valley-shaped recesses 75a, 75b and 75c are formed. With this configuration, at the time of discharging from space 60 to the outer periphery surface of probe 11, discharging of liquid is easily achieved by the increase in pressure when a biological tissue enters space 60. Meanwhile, at the time when liquid flows back to space 60 from the outer periphery surface of probe 11, since no pressure is applied from the outer periphery surface of probe 11, advancement of the liquid is hindered and a reverse flow does not easily occur because of the effect of the surface tension generated by the form of the corner portion composed of protrusions 74a and 74b, and recesses 75a, 75b and 75c. That is, it is possible to prevent part of liquid which has discharged out of space 60 from returning back to space 60 due to the surface tension. It is to be noted that, preferably, protrusions 74a and 74b and recesses 75a, 75b and 75c each has a square form to effectively prevent the reverse flow of liquid.

In addition, a similar effect can be achieved with the configuration in which protrusions 74a and 74b in the form of projection, and recess 75a in the form of a flat surface are provided to the bottom surface of liquid ejection trench 61 as illustrated in FIG. 17C.

Figure 18A:
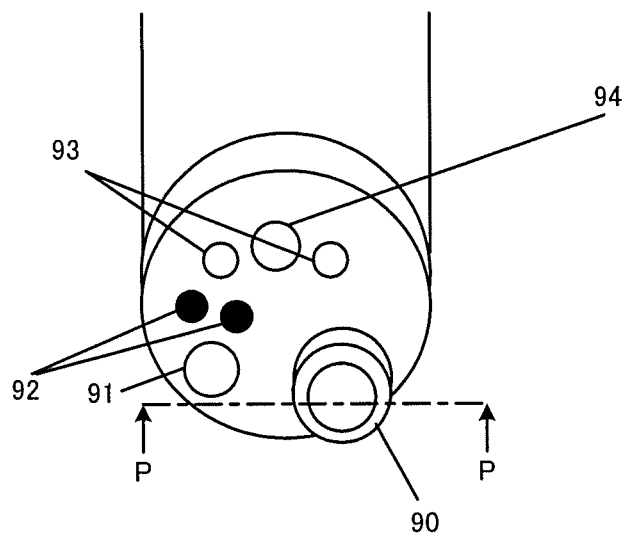
FIGS. 18A and 18B illustrate a modification of the configuration of the probe distal end portion according to the embodiment of the present invention.
Figure 18B:
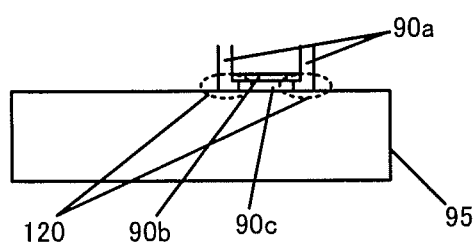
Figure 19:
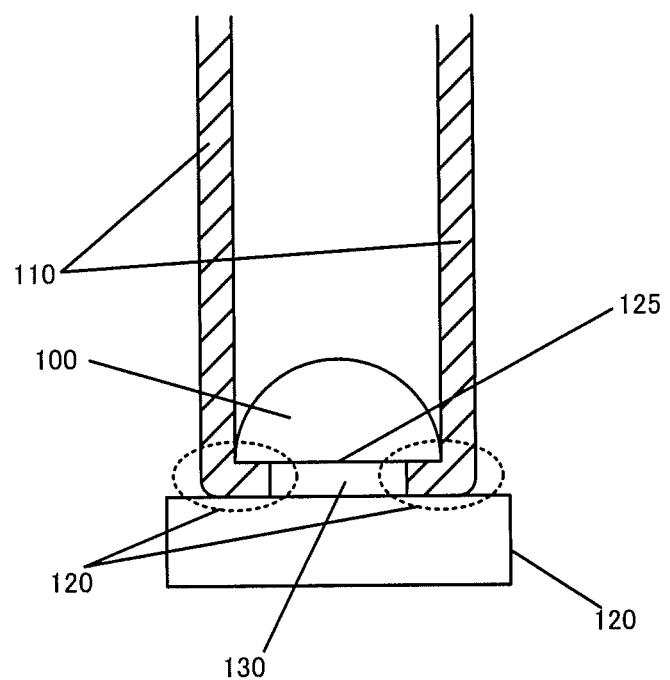
FIG. 19 illustrates a problem of a conventional technique.

In addition, while probe 11 is incorporated in endoscope main body 2 in the above-mentioned embodiment, the present invention is not limited to this. For example, the function of probe 11 may be incorporated in a confocal endoscope. A confocal endoscope irradiates an observation object part in a lumen with laser light, and receives reflection light for visualization. FIG. 18A illustrates a configuration of a distal end portion of a confocal endoscope. FIG. 18B is a sectional view taken along line P-P of FIG. 18A. As illustrated in FIG. 18A, at the distal end portion of the confocal endoscope, a tubular distal end protruding section (confocal scanning section) 90 functioning as probe 11, forceps channel 91, air-and-water supply nozzle 92, light guide 93, CCD camera 94 and the like are provided.

As illustrated in FIG. 18B, slide glass 90b as an optical member is fitted in the distal end of distal end protruding section 90. In addition, at the distal end of distal end protruding section 90, holding section 90a having space 90c whose internal diameter is smaller than the internal diameter of distal end protruding section 90 is provided. Holding section 90a is provided with catch 120, thus preventing slide glass 90b from dropping off from distal end protruding section 90. However, because of the thickness of catch 120, space 90c is defined between the distal end surface of slide glass 90b in the form of a planar surface, and an observation object part of biological tissue 95. For this reason, holding section 90a is provided with any of the above-described liquid ejection trenches that connects space 90c and the outer periphery surface of distal end protruding section 90. With this configuration, it is possible to ensure a path through which liquid of biological tissue 95 having entered space 90c is discharged from space 90c, at the time when laser light is applied to an observation object part of biological tissue 95.

In addition, while an exemplary case has been mainly described in which probe 11 is inserted into the body via endoscope main body 2 in the above-mentioned embodiment, the present invention is not limited thereto. For example, it is also possible to apply to the above-described confocal endoscope, and probe 11 may be independently inserted into the body.

The embodiments disclosed herein are merely exemplifications and should not be considered as limitative. While the invention made by the present inventor has been specifically described based on the preferred embodiments, it is not intended to limit the present invention to the above-mentioned preferred embodiments but the present invention may be further modified within the scope and spirit of the invention defined by the appended claims.

This application is entitled to and claims the benefit of Japanese Patent Application No. 2012-055673 dated Mar. 13, 2012, the disclosure of which including the specification, drawings and abstract is incorporated herein by reference in its entirety.

REFERENCE SIGNS LIST

1 Endoscope system
2 Endoscope main body
3 Endoscope device
4 Diagnosis device
5, 6 Input device
7, 8 Monitor
11 Probe
11a Probe proximal end portion
11b Probe distal end portion
21 Introduction portion
21a Proximal end portion
21b Distal end portion
21c Operable section
22 Operation section
22a Nob
23 Cable
31 Illuminating light source
32 Image processing section
33 CPU
41 Light source
42 Spectroscope
43 CPU
45 Storage device
50 Excitation light fiber
52, 52a, 52b, 52c Light receiving fiber
54 Lens
56, 67 Holding section
58, 120 Catch
60 Space 61, 62, 63, 64, 65, 66, 68, 69, 70 Liquid ejection trench
71*a*, 71*b*, 71*c*, 71*d* Liquid
72, 73 Liquid housing section
74*a*, 74*b* Protrusion
75*a*, 75*b*, 75*c* Recess
90 Distal end protruding section
90*a* Holding section
90*b* Slide glass
90*c* Space
91, CH forceps channel
92 Air-and-water supply nozzle
93, LG Light guide
94 CCD camera
95 Biological tissue
CA Camera

The invention claimed is:

1. A probe in which an optical member is fitted in a distal end of a tubular member that is insertable to a lumen, the probe being configured to irradiate a measurement object part in the lumen with light and to acquire measurement light radiated from the measurement object part, wherein the probe comprises:
    a holding section including a space having an internal diameter smaller than an internal diameter of the tubular member is provided at the distal end of the tubular member;
    a liquid ejection trench configured to connect the space and an outer periphery surface of the holding section is formed in the holding section;
    an excitation light fiber configured to irradiate the measurement object part with excitation light;
    a light receiving fiber configured to receive measurement light radiated from the measurement object part; and
    a lens provided as the optical member, the lens being provided in front of the excitation light fiber and the light receiving fiber in such a manner as to face a distal end side of the tubular member,
    wherein an axial end portion of at least one of the excitation light fiber and the light receiving fiber is disposed at a position corresponding to an opening part of the liquid ejection trench on the space side of the holding section.

2. The probe according to claim 1, wherein one liquid ejection trench is formed in the holding section.

3. The probe according to claim 1, wherein two or more liquid ejection trenches are formed in the holding section.

4. The probe according to claim 1, wherein the liquid ejection trench is formed in a tapered form whose width increases or decreases from the space side toward the outer periphery surface of the holding section.

5. The probe according to claim 1, wherein a tapered surface having a dent form whose depth increases toward an inside in a radial direction of the holding section is provided to a surface of the holding section which faces the measurement object part.

6. The probe according to claim 1, wherein, in a bottom portion of the liquid ejection trench, a stepped groove whose depth increases toward a center portion in the width direction of the liquid ejection trench is continuously formed along an extending direction of the liquid ejection trench.

7. The probe according to claim 1, wherein the liquid ejection trench has a cross-sectional shape cut out in a V-shape whose width decreases toward a bottom portion.

8. The probe according to claim 1, wherein a liquid housing section in communication with the liquid ejection trench is formed in the holding section.

9. The probe according to claim 1, wherein a protrusion and a recess are formed in a bottom surface of the liquid ejection trench.

* * * * *